(12) United States Patent
Donoghue et al.

(10) Patent No.: US 9,107,938 B2
(45) Date of Patent: Aug. 18, 2015

(54) METHODS OF SELECTING AND USING THERAPEUTIC AND PROPHYLACTIC PROBIOTIC CULTURES TO REDUCE BACTERIAL PATHOGEN LOADS

(75) Inventors: Daniel James Donoghue, Fayetteville, AR (US); Ann Marian Donoghue, Fayettevile, AR (US)

(73) Assignees: The Board of Trustees of the University of Arkansas, Little Rock, AR (US); The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/876,743

(22) PCT Filed: Sep. 30, 2011

(86) PCT No.: PCT/US2011/054312
§ 371 (c)(1),
(2), (4) Date: Apr. 16, 2013

(87) PCT Pub. No.: WO2012/044984
PCT Pub. Date: Apr. 5, 2012

(65) Prior Publication Data
US 2013/0323218 A1    Dec. 5, 2013

Related U.S. Application Data (60) Provisional application No. 61/388,034, filed on Sep. 30, 2010.

(51) Int. Cl.
*C12Q 1/06* (2006.01)
*A61K 35/741* (2015.01)
(Continued)

(52) U.S. Cl.
CPC ............. *A61K 35/741* (2013.01); *A23L 1/3014* (2013.01); *A61K 35/74* (2013.01); *C12N 1/20* (2013.01); *C12Q 1/02* (2013.01); *A61K 2035/11* (2013.01)

(58) Field of Classification Search
IPC ................................................ C12Q 1/06,1/10
See application file for complete search history.

(56) References Cited

U.S. PATENT DOCUMENTS

| | | | |
|---|---|---|---|
| 3,682,842 | A | 8/1972 | Innerfield |
| 4,279,995 | A | 7/1981 | Woods et al. |

(Continued)

FOREIGN PATENT DOCUMENTS

| | | |
|---|---|---|
| CN | 101569375 A | 11/2009 |
| CN | 101580799 A | 11/2009 |

(Continued)

OTHER PUBLICATIONS

Gemmell, The physiological characters and flagellar arrangement of motile homofermentative *Lactobacilli*, J Gen Microbiol 35:519-528, 1964.*

(Continued)

*Primary Examiner* — Rosanne Kosson
(74) *Attorney, Agent, or Firm* — Andrus Intellectual Property Law, LLP (57) ABSTRACT

Methods are provided for selecting a bacterium capable of reducing pathogenic bacterial colonization of the intestinal tract in a subject comprising selecting the bacterium capable of migrating at least 0.75 cm from the point of inoculation on motility agar after incubation for 24 hours at 37° C. or capable of migrating from the point of inoculation to a diameter of at least 1.5 cm based on the farthest colonies from the point of inoculation on motility agar after incubation for 24 hours at 37° C. Bacteria selected using the method and compositions comprising these bacteria are also provided.

8 Claims, 3 Drawing Sheets

(51) Int. Cl.

| | | |
|---|---|---|
| A61K 35/74 | (2015.01) | |
| C12N 1/20 | (2006.01) | |
| A23L 1/30 | (2006.01) | |
| C12Q 1/02 | (2006.01) | |
| A61K 35/00 | (2006.01) | |

(56) References Cited

U.S. PATENT DOCUMENTS

| | | |
|---|---|---|
| 4,335,107 A | 6/1982 | Snoeyenbos et al. |
| 4,657,762 A | 4/1987 | Mikkola et al. |
| 4,689,226 A | 8/1987 | Nurmi et al. |
| 5,208,150 A | 5/1993 | Tate et al. |
| 5,296,221 A | 3/1994 | Mitsuoka et al. |
| 5,401,501 A | 3/1995 | Pratt |
| 5,451,400 A | 9/1995 | Stern et al. |
| 5,466,445 A | 11/1995 | Hunter |
| 5,478,557 A | 12/1995 | Nisbet et al. |
| 5,612,055 A | 3/1997 | Bedford et al. |
| 5,807,546 A | 9/1998 | Stern et al. |
| 5,824,322 A | 10/1998 | Balasubramanian |
| 5,951,977 A | 9/1999 | Nisbet et al. |
| 6,010,695 A | 1/2000 | Line et al. |
| 6,017,525 A | 1/2000 | Logan et al. |
| 6,107,525 A | 8/2000 | Dakka et al. |
| 6,110,455 A | 8/2000 | Hargis et al. |
| 6,136,554 A | 10/2000 | Bochner |
| 6,214,335 B1 | 4/2001 | Stern et al. |
| 6,461,607 B1 | 10/2002 | Farmer |
| 6,797,266 B2 | 9/2004 | Naidu |
| 6,805,852 B2 | 10/2004 | Lin et al. |
| 7,063,836 B2 | 6/2006 | Garner et al. |
| 7,247,299 B2 | 7/2007 | Lin et al. |
| 7,294,337 B2 | 11/2007 | Fioramonti et al. |
| 7,700,094 B1 | 4/2010 | Nsereko et al. |
| 7,708,988 B2 | 5/2010 | Farmer |
| 7,754,469 B2 | 7/2010 | Baltzley et al. |
| 2001/0018048 A1 | 8/2001 | Leer et al. |
| 2002/0146399 A1 | 10/2002 | Raczek |
| 2003/0031659 A1 | 2/2003 | Farmer |
| 2003/0039703 A1 | 2/2003 | Anderson et al. |
| 2003/0175305 A1 | 9/2003 | Garner et al. |
| 2003/0180260 A1 | 9/2003 | Clancy et al. |
| 2004/0101525 A1 | 5/2004 | Lin et al. |
| 2004/0241150 A1 | 12/2004 | Hargis et al. |
| 2005/0084500 A1 | 4/2005 | Molly et al. |
| 2005/0244389 A1 | 11/2005 | Fioramonti et al. |
| 2005/0271643 A1 | 12/2005 | Sorokulova et al. |
| 2006/0034814 A1* | 2/2006 | Doyle et al. ............... 424/93.45 |
| 2006/0099197 A1 | 5/2006 | Farmer |
| 2006/0099229 A1 | 5/2006 | Ravichandran et al. |
| 2006/0134082 A1 | 6/2006 | Baillon et al. |
| 2007/0148146 A1 | 6/2007 | Doyle et al. |
| 2008/0009414 A1 | 1/2008 | Ho et al. |
| 2008/0044501 A1 | 2/2008 | Lee et al. |
| 2008/0057047 A1 | 3/2008 | Sas et al. |
| 2008/0085268 A1 | 4/2008 | Fioramonti et al. |
| 2008/0233104 A1 | 9/2008 | Farmer |
| 2009/0257995 A1 | 10/2009 | Mochizuki |
| 2010/0074873 A1 | 3/2010 | Watson |
| 2010/0074994 A1 | 3/2010 | Harel et al. |
| 2010/0092428 A1 | 4/2010 | Schmidt et al. |

FOREIGN PATENT DOCUMENTS

| | | |
|---|---|---|
| EP | 2 011 858 A1 | 1/2009 |
| RU | 2 203 947 C1 | 5/2003 |
| WO | WO 88/06619 | 9/1988 |
| WO | WO 2004/044186 | 5/2004 |
| WO | WO 2005/019417 | 3/2005 |
| WO | WO 2010/068231 | 6/2010 |
| WO | WO 2012/009712 | 1/2012 |

OTHER PUBLICATIONS

Hibbard et al., "A *Bacillus*-based direct fed microbial probiotic reduces *Salmonella* spp. isolation from the litter of broiler chickens," ASM 109th General Meeting, Abstract No. P-033, 2009.*

Swine Nutrition, 2nd ed., A. J. Lewis and L. L. Southern, Eds., CRC Press, LLC, Boca Raton, 2001. pp. 404-405.*

Abdollahi, M.R. et al., "Effect of different levels of bacterial probiotic on broilers performance," Animal Science Department, College of Agiculture, University of Tehran, Karaj-Iran.

Aguiar, V.F. et al., "Targeting motility properties of bacteria in the development of probiotic cultures against *Campylobacter jejuni* in broiler chickens," (2013) Foodborne Pathog Dis. 10(5):435-441.

Alexopoulos, C. et al., "Field evaluation of the effect of a probiotic-containing *Bacillus licheniformis* and *Bacillus subtilis* spores on the health status, performance, and carcass quality of grower and finisher pigs," (2004) Journal of Veterinary Medicine Series A Physiol Pathol Clin Med 51(6):306-312.

Alexopoulos, C. et al., "Field evaluation of the efficacy of a probiotic containing *Bacillus licheniformis* and *Bacillus subtilis* spores, on the health status and performance of sows and their litters,"0 (2004) Journal of Animal Physiology and Animal Nutritions 88(11-12):381-392 (Abstract).

Anderson, R.C. et al., "Effect of competitive exclusion on transmission of *Salmonella choleraesuis* between early weaned pigs," (1999) ISECSP: Detection/Host-Agent Ineraction, pp. 18-21.

Farnell, M.B. et al., "*Campylobacter* susceptibility to ciprofloxacin and corresponding fluoroquinolone concentrations within the gastrointestinal tracts of chickens," (2005) J. Applied Microbiology 99:1043-1050.

Hong, H.A. et al., "The use of bacterial spore formers as probiotic" (2005) FEMS Microbiol Rev 29(4):813-835 Epub Dec. 16, 2004.

Kowalski, Z.M. et al., "Performance of Holstein calves fed milk-replacer and starter mixture supplemented with probiotic feed additive," (2009) Journal of Animal and Feed Sciences 18:399-411.

Kritas, S.K. et al., "Effect of *Bacillus licheniformis* and *Bacillus subtilis* supplementation of ewe's feed on sheep milk production and young lamb mortality," (2006) Journal of Veterinary Medicine Series A Physiol Pathol Clin Med 53(4):170-173.

Link, R. et al., "Composition of sow's milk and selected metabolic indices after administration of probiotics," (2007) Research in Pig Breeding 1(1):40-42.

Mahdavi, A.H. et al., "Effect of probiotic supplement on egg quality and laying hen's performance," (2005) International Journal of Poultry Science 4(7):488-492.

Mahdavi, A.H. et al., "Effect of probiotic inclusion in different levels of barley subsitution for corn diets on egg quality and laying hen's performance," (2005) Pakistani Journal of Biological Sciences 8(11):1521-1528.

Mutus, R. et al., "The effect of dietary probiotic supplementation on tibial bone characteristics and strength in broilers," (2006) Poultry Science 85(9):1621-1625.

Nurmi, E. et al., "New aspects of *Salmonella* infection in broiler production," (1973) Nature 241:210-211.

Pelicano, E.R.L. et al., "Effect of different probiotics on broiler carcass and meat quality," (2003) Brazilian Journal of Poultry Science 5(3)207-214.

Sabatkova, J. et al., "The probiotic BioPlus 2B as an alternative to antibiotics in diets for broiler chickens," (2008) ACTA VET, BRNO 77:569-574.

Wolfenden, R.E., Evaluation of a screening and selection method of *Bacillus* isolates for use as effective direct-fed microbials in commerial poultry, (2010) International Journal of Poultry Science 9(3):317-323.

International Search Report and Written Opinion for International Patent Application No. PCT/US2011/054312 dated Jan. 26, 2012 (15 pages).

\* cited by examiner

METHODS OF SELECTING AND USING THERAPEUTIC AND PROPHYLACTIC PROBIOTIC CULTURES TO REDUCE BACTERIAL PATHOGEN LOADS

CROSS REFERENCE TO RELATED APPLICATIONS

This patent application is a national stage filing under 35 U.S.C. 371 of International Application No. PCT/US2011/054312 filed Sep. 30, 2011, which claims the benefit of priority oft United States Provisional Patent Application No. 61/388,034, filed Sep. 30, 2010, both of which are incorporated herein by reference in their entirety.

BACKGROUND

*Campylobacter* is one of the most commonly reported bacterial causes of human food-borne illness in the United States and epidemiological evidence indicates poultry and poultry products as a significant source of human *Campylobacter* infection. Colonization of poultry by *Campylobacter* is widespread and difficult to prevent even with proper biosecurity measures. *Campylobacter* is considered a commensal organism in avian species and it is predominantly found in the lower gastrointestinal tract of birds, concentrated in the mucus layer of the cecal crypts, cloaca and large intestine. The evisceration techniques at the processing plant are usually the most common source of carcass contamination with *Campylobacter*.

Reducing *Campylobacter* in the intestinal tract would reduce contamination of poultry products. A variety of approaches for reducing the colonization of *Campylobacter* in poultry have been explored, but with varying degrees of success. These include use of enzymes such as xylanase, bacteriophage, bacteriocins, frutooligosaccharides and mucin utilizing coliforms, organic acids and antibiotics.

Another approach to decrease food-borne pathogens and minimize the use of antibiotics is by the use of competitive exclusion (CE) microflora. Also known as probiotics, CE was first introduced by Nurmi and Rantala (Nature (1973) 241: 210-211). Probiotics are composed of single or mixtures of selected non-pathogenic organisms that upon ingestion have the ability to colonize the gastrointestinal tract and improve the hosts' health. Probiotics are usually given orally at day-of-hatch/birth allowing these bacteria to first colonize the intestinal tract before the bird/animal is exposed to pathogenic microorganisms present in the environment. The probiotic cultures used for poultry are generally obtained from intestinal tracts of healthy young birds. Undefined probiotic cultures cannot assure the absence of pathogenic organisms, guarantee the same strains are present for every treatment; and are not approved by regulatory agencies for use in the U.S. Nonetheless, the "Nurmi concept" has been demonstrated to be an effective means in reducing *Salmonella* colonization in broilers. Although the results to date are promising against *Salmonella*, *Campylobacter* has presented a more difficult target.

SUMMARY

Methods of selecting bacterial strains capable of inhibiting the growth or colonization capability of pathogenic bacteria and several of the selected bacterial strains are provided herein. Methods of using these selected strains are also provided and several strains selected by the methods are provided.

In one aspect, methods of selecting a first bacterium capable of reducing bacterial colonization, in particular pathogenic bacterial colonization, of the intestinal tract of a subject are provided. The methods include selecting bacteria with enhanced motility relative to controls of the same species. In particular, bacteria capable of reducing pathogenic bacterial colonization of the intestinal tract in a subject by selecting the first bacterium capable of migrating at least 0.75 cm from the point of inoculation on motility agar after incubation for 24 hours at 37° C. or capable of migrating from the point of inoculation to a diameter of at least 1.5 cm based on the farthest migrating bacterial colonies from the point of inoculation on motility agar after incubation for 24 hours at 37° C. are selected. The bacteria may be further selected to include those bacteria Generally Recognized as Safe by the Food and Drug Administration.

In another aspect, the bacteria selected by the methods described herein and compositions comprising the bacteria are described.

In yet another aspect, isolated *Bacillus subtilis* strains designated as ME-1, ME-2 and ME-3 are provided. Compositions, such as probiotic food products or nutraceuticals, comprising the isolated *Bacillus subtilis* strains or other bacterial isolates selected by the methods are also provided.

In still another aspect, methods of inhibiting growth of pathogenic bacteria are provided. The methods include delivering a bacterium selected by the methods described herein and having enhanced motility or at least one of the *Bacillus subtilis* strains ME-1, ME-2 or ME-3, a combination thereof or a composition comprising at least one of the bacterium selected by the methods described herein or one of the *Bacillus subtilis* strains (ME-1, ME-2 or ME-3) to a target region.

In a still further aspect, methods of reducing pathogenic bacterial colonization in a subject are provided. The methods include oral administration of a bacterium selected by the methods described herein and having enhanced motility or at least one of the *Bacillus subtilis* strains ME-1, ME-2 or ME-3, a combination thereof or a composition comprising at least one of the bacterium selected by the method described herein or one of the *Bacillus subtilis* strains (ME-1, ME-2 or ME-3) to the subject.

DETAILED DESCRIPTION

Figure 1:
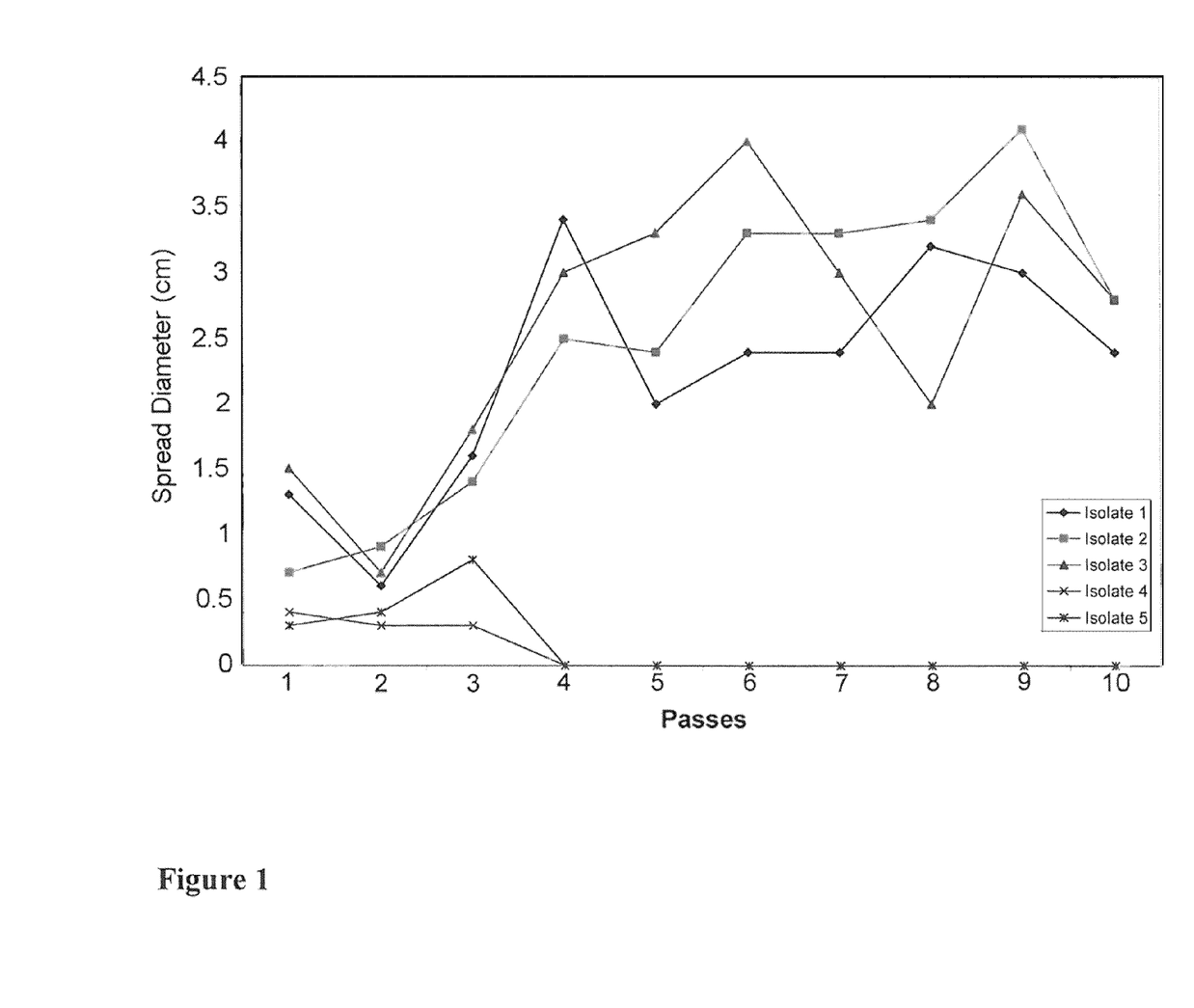
FIG. 1 is a graph showing the diameter of spread after each subsequent selection and passage for motility enhancement of the bacterial isolates.
Figure 2:
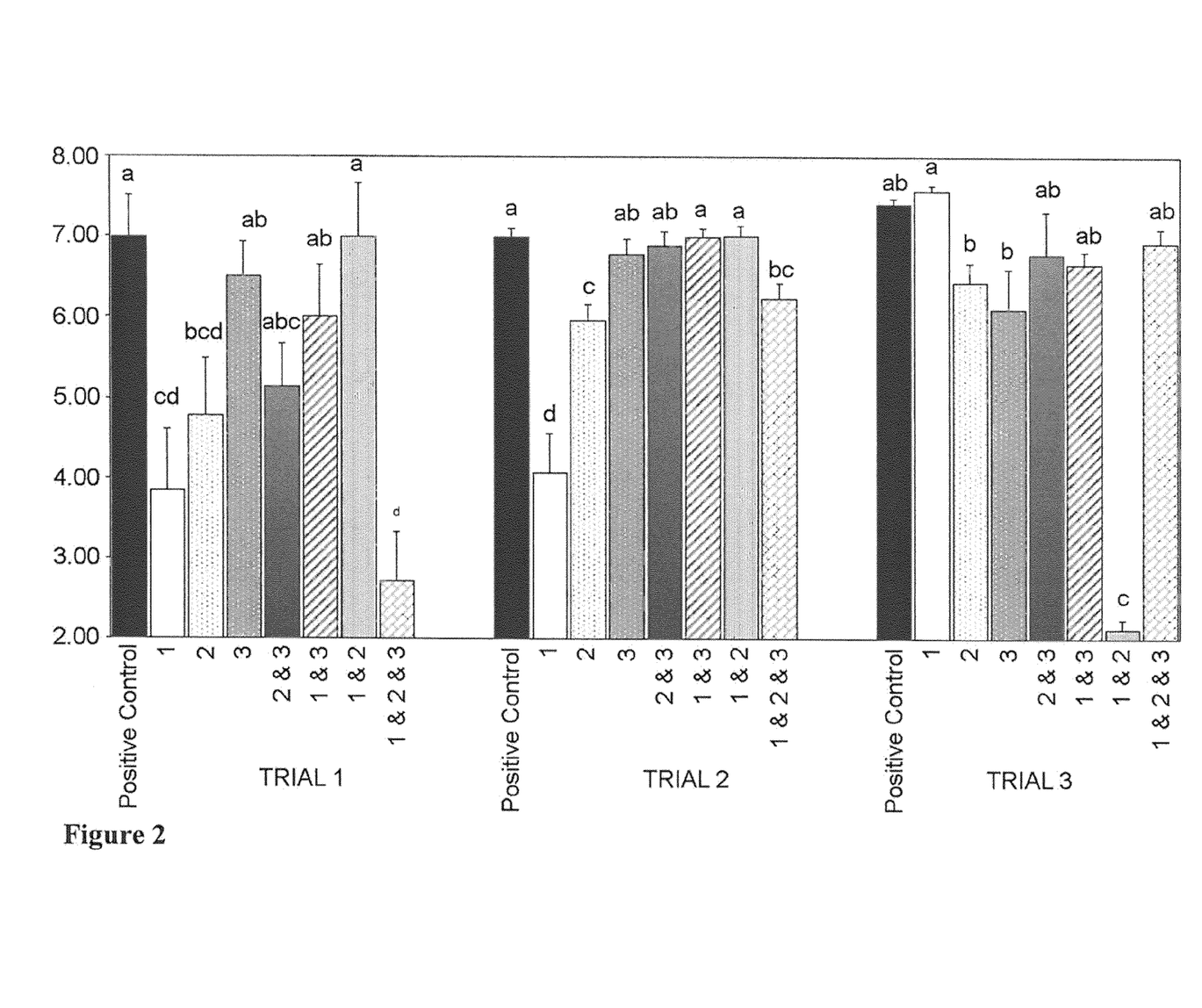
FIG. 2 is a graph showing the concentration of *Campylobacter* per gram of cecal contents seven days after inoculation with *Campylobacter* in two week old chicks that were either not treated with a probiotic or were treated on the day of hatch with the indicated isolates or combinations of isolates. Three separate trials are shown and columns within the same trial with different superscripts denote significant difference ($P<0.05$).
Figure 3:
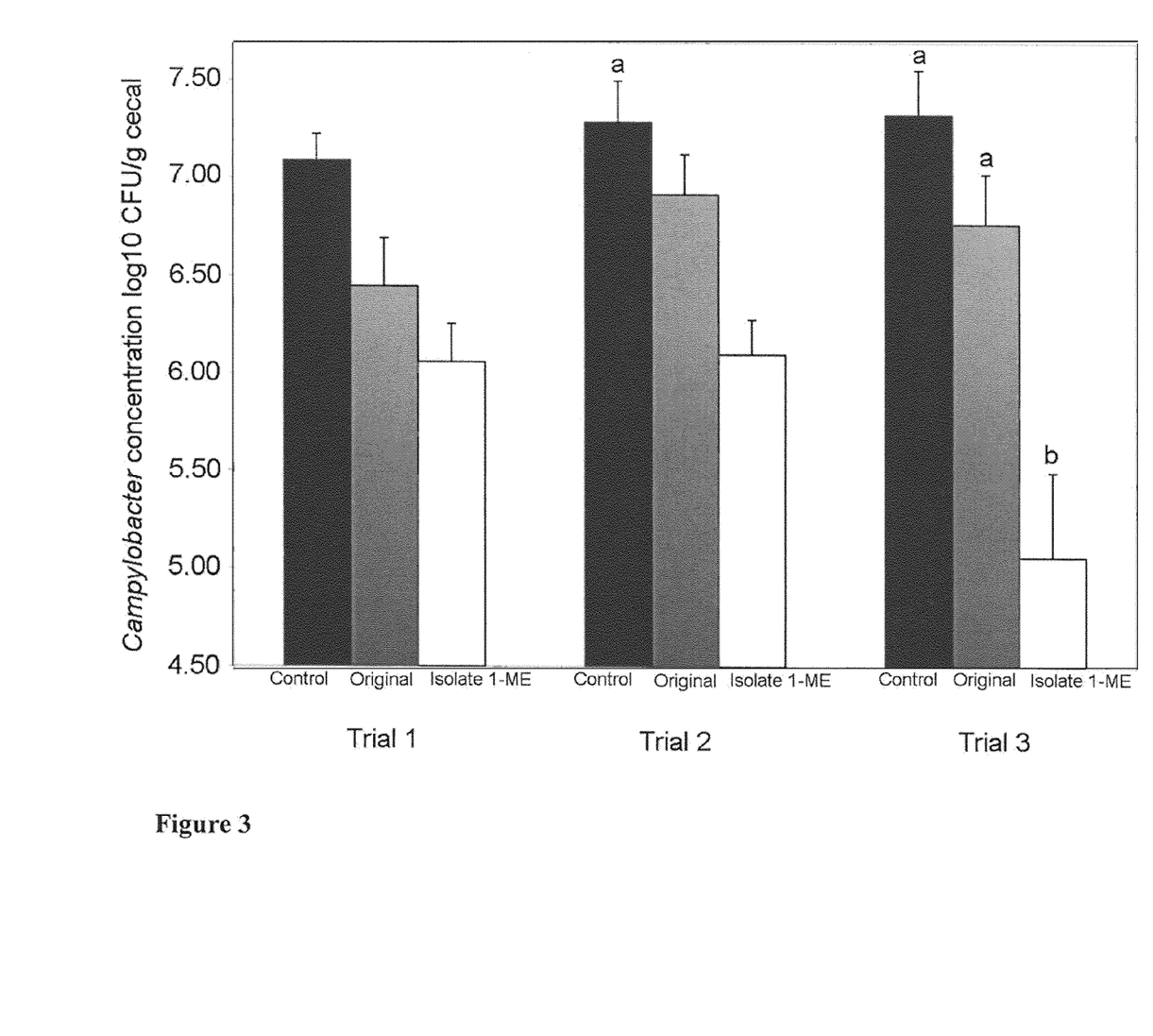
FIG. 3 is a graph showing the concentration of *Campylobacter* per gram of cecal contents seven days after inoculation with *Campylobacter* in two week, old chicks. The chicks were either not treated with a probiotic (control) or were treated on the day of hatch with the original isolate 1 or with the motility enhanced isolate 1. Three separate trials are shown and columns within the same trial with different superscripts denote significant difference ($P<0.05$).

*Campylobacter* is a pathogenic bacterium that is a leading cause of food-borne illness. *Campylobacter* infection is often associated with the consumption of poultry products. *Campylobacter* is commonly present in the intestinal tract of poultry and one strategy to reduce enteric colonization is the use of probiotic cultures. Such probiotic cultures have been developed and shown to be effective to reduce colonization of *Salmonella*, but the results for *Campylobacter* have not been promising.

As described in the Examples, we discovered that selection of bacteria for enhanced motility resulted in selection of bacteria capable of reducing colonization of other pathogenic bacteria in a subject such as *Campylobacter*. The isolated bacteria were selected based on initial motility and were then further selected by serial passage on motility agar selecting the most motile isolates to select for enhanced motility. Those bacteria with motility characteristics that may be useful to reduce colonization by pathogenic bacteria in a subject were bacteria capable of migrating at least 0.75 cm, 1 cm, 1.5 cm or even 2 cm from the point of inoculation on motility agar after incubation for 24 hours at 37° C. or capable of migrating from the point of inoculation to a diameter (to form a zone of migration with a diameter) of at least 1.5 cm, 2 cm, 3 cm, or even 4 cm based on the farthest migrating bacterial colonies from the point of inoculation on motility agar after incubation for 24 hours at 37° C. are selected. Motility agar from Becton-Dickinson was used in the Examples. Those skilled in the art will appreciate that other bacterial motility media are available and can be used to develop similar assays.

As described in the Examples, three strains of *Bacillus subtilis* were selected for enhanced motility and were demonstrated to inhibit *Campylobacter* growth in vitro and in vivo in chickens. The three strains are designated ME-1, ME-2 and ME-3 (ME: motility enhanced). These three strains or other similar isolates selected using the methods disclosed herein may be used to make probiotic compositions that contain at least one of the isolates or any combination thereof. The compositions may also contain bacterial strains in addition to those disclosed herein. The compositions may be used in food products, as additives to drinking water or in nutraceuticals or pharmaceuticals. Thus, food products, additives and nutraceuticals including at least one of ME-1, ME-2 or ME-3 or any other bacteria selected using the method of selection described herein are provided.

As described in the Examples, the three strains were selected by harvesting bacteria from the ceca of two week old chickens and then identifying those isolates Generally Recognized as Safe (GRAS) based on the Food and Drug Administration (FDA) list; identifying which of these GRAS isolates demonstrated motility characteristics (6 isolates); and finally determining which of the motile, GRAS isolates were capable of inhibiting *Campylobacter* growth in vitro (5 isolates). The five isolates were then subjected to serial passage and selection for new isolates with the greatest motility. Three of the isolates demonstrated improved motility with serial passage and selection and these three isolates are now designated as ME-1, ME-2 and ME-3.

Thus a novel method for selection and isolation of bacterial strains capable of inhibiting growth and/or colonization of pathogenic bacteria in the gastrointestinal tract of a subject, such as *Campylobacter* in vitro and in vivo, is provided. The pathogenic bacteria include bacteria that are capable of causing disease, e.g., morbidity or mortality, in humans. These pathogenic bacteria may cause no significant disease in the host or subject being treated or administered the probiotic compositions. For example, *Campylobacter* and *Salmonella* are commensal organisms in chickens and generally do not cause disease in chickens, but both represent major sources of food-borne illness in humans and thus are considered pathogenic organisms herein. Pathogenic organisms also include organisms that cause disease in the host or subject being treated or administered the composition comprising the bacteria selected using the methods described herein or any of the three isolates provided, namely ME-1, ME-2 or ME-3.

The bacteria selected for their ability to inhibit the growth or colonization of pathogenic bacteria may be from any genera of bacteria. The selected bacteria are suitably enteric bacteria that are part of the normal gut flora of the animal or of the subject being treated. As noted above, the selected bacteria may also be normal gut floral of a human. Suitably, the selected bacteria are further selected to include GRAS bacteria. Suitably, the selected bacteria are from genera such as *Escherichia, Salmonella, Shigella, Bacillus, Clostridium* and *Bacteriodes*.

The methods include selecting a bacterium with enhanced motility relative to an unselected bacterium of the same species. Suitably the bacteria may be selected for enhanced motility relative to bacteria in the same culture or even from the same isolate via serial passage and selection of bacteria from the culture or isolate that have the greatest motility from the point of inoculation. The bacteria may be selected by the ability to migrate a particular distance from an inoculation point or to produce a zone of migration having a certain diameter. Suitably, the selected bacteria are capable of migrating from the inoculation point at least 0.5 cm, more suitably the distance is at least 0.75 cm, 0.9 cm, 1.0 cm, 1.2 cm, 1.4 cm, 1.6 cm, 1.8 cm or 2.0 cm by 24 hours after inoculation when incubated at 37° C. on a motility agar such as BBL Motility medium from Becton-Dickinson. The bacteria may be selected by the diameter of the zone of migration as an alternative. Suitably, the selected bacteria are capable of migrating such that the the diameter of the zone of migration is at least 1.0 cm, 1.2 cm, 1.4 cm, 1.6 cm, 1.8 cm, 2.0 cm, 2.2 cm, 2.5 cm, 2.7 cm, 3.0 cm, 3.2 cm, 3.5 cm, 3.7 cm, or 4.0 cm by 24 hours after inoculation when incubated at 37° C. on a motility agar such as BBL Motility medium from Becton-Dickinson.

The bacteria capable of reducing pathogenic bacterial colonization of the intestinal tract of a subject may also be selected using additional criteria. The bacteria may be further selected using the FDA GRAS classification scheme, such that only bacteria approved as GRAS are selected. Those of skill in the art will appreciate that bacterial characterization may be accomplished using commercially available bacterial typing technology such as the Biolog system used in the examples or may be accomplished using traditional bacterial typing techniques including microscopic characterization using stains, differential growth or colorimetric staining on different growth media or other PCR or DNA typing based methodologies.

The bacteria may be further selected for their ability to inhibit the growth of pathogenic bacteria, such as *Campylobacter, Salmonella*, or *E. coli*, in vitro. The ability to inhibit the growth of pathogenic bacteria may be measured in a variety of ways, one of which is described in the Examples. The ability of the bacteria to create a zone of inhibition of growth of the pathogenic bacteria when plated in discreet locations on a plate confluent for the pathogen is one way of measuring the ability to inhibit growth of a pathogen in vitro. Those of skill in the art will appreciate that similar assays can be performed in solution.

The bacteria may also be selected for their ability to reduce colonization of pathogenic bacteria in a subject. The pathogenic bacteria may be *Salmonella, E. coli* or *Campylobacter*. The subjects may be poultry (including chicken and turkeys), cattle, pigs, mice, rats, humans or other domesticated animals or pets such as dogs, cats, lizards, snakes. In the Examples, ME-1, ME-2 and ME-3 were tested for their ability to reduce *Campylobacter* colonization in chickens. The motility enhanced bacterial isolates were orally administered (by oral gavage) to day of hatch chicks. Two weeks later the chicks were administered a mixture of *Campylobacter* isolates. After an additional two weeks the chicks were sacrificed, ceca harvested and *Campylobacter* concentration in the ceca determined. The motility enhanced bacteria were capable of reducing the colonization of the chicken ceca with *Campylobacter*. Similar results are expected with other pathogenic bacteria such as *Salmonella* and *E. coli*.

The methods of selecting bacteria capable of reducing bacterial colonization of the intestinal tract described herein may be readily applied by those of skill in the art to isolate other bacteria capable of reducing colonization by pathogenic bacteria. For Example, bacteria may be harvested from the intestinal tract of cattle and selected for enhanced motility as described herein to select for bacteria capable of reducing pathogenic bacterial colonization of cattle. The pathogenic bacteria may be *Salmonella* or *E. coli* as well. Alternatively, bacteria may be selected from one species and used to treat another. For example, ME-1 was selected from a chicken but may be used to treat an animal other than a chicken such as a turkey or cow.

Compositions comprising the bacteria selected using the methods described above are provided. The compositions may include a pharmaceutically acceptable carrier, diluent and/or excipient. The composition may include more than one bacterial isolate selected by the methods described herein or may also include other bacterial isolates. The compositions may be formulated for delivery in food, water, via oral gavage or via an aerosol or sprayable product.

Methods of inhibiting growth of pathogenic bacteria by delivering a composition including a bacteria selected by the methods described herein or at least one of the strains described herein (ME-1, ME-2 or ME-3) or a composition comprising at least one of the strains to a target region are provided. The strains may be delivered singly or in combination with other strains including those described herein and those not disclosed herein or selected using other methods. The target region may be within a solution, in an area, on a surface, an object or a subject suspected of being contaminated with, harboring or being susceptible to contamination with a pathogenic bacterium.

Delivery of a composition containing a bacterium selected by the methods described herein or one or more of the described bacterial isolates, ME-1, ME-2 or ME-3 allows the growth of the pathogenic bacteria to be inhibited or reduced as compared to a control. A suitable control would be a similar target region to which the bacterial strains disclosed herein or a composition comprising the ME-1, ME-2 or ME-3 strains were not delivered. The bacteria described herein may actively inhibit pathogenic bacterial growth, but need not do so. The reduction or inhibition of growth of or colonization by the pathogenic bacteria may be accomplished through any other means, including outcompeting the pathogenic bacteria for the niche in which the bacteria colonize and/or grow in the subject. The growth of the pathogenic bacteria may be inhibited or reduced as compared to untreated controls by 2-fold, 5-fold, 10-fold, 15-fold, 20-fold, 25-fold, 30-fold, 40-fold, 50-fold or even by as much as 2 logs, 3 logs or 4 logs. Growth inhibition may be measured by any means, including those known to those of skill in the art, such as plating for colony forming units, real-time PCR, and spectroscopic determination.

The strains or compositions may be delivered to the target region using a variety of methods. Suitably, the bacterial strains or compositions comprising them are added directly to the target region. Delivery may include mixing, direct contact, or may rely on processes such as diffusion. Alternatively, the strains or compositions may be mixed with a solution prior to delivery to the target region to facilitate the delivery. The compositions may be used to treat subjects but may also be used to treat surfaces or objects that subjects may come into contact with and form a source of potential infection by pathogens.

Methods of reducing pathogenic bacterial contamination in the gastrointestinal tract of a subject are also provided. These methods include orally administering a bacteria selected using the methods described herein or at least one of ME-1, ME-2, ME-3 or a composition comprising at least one of these strains to the subject. The subjects include but are not limited to poultry such as chickens and turkeys, cattle, humans, pigs, mice, rats, cats, dogs or other domesticated animals or pets. As noted above the pathogenic bacteria may include, but are not limited to *Campylobacter, Salmonella* and *E. coli*.

The strains or compositions described herein may be administered in a variety of ways known or available to those skilled in the art. The strains or compositions may be administered via oral gavage as described in the examples, or alternatively may be administered in the form of a pharmaceutical, nutraceutical, added to the food or water or provided in aerosolized or sprayable form for administration by inhalation. In addition, the strains and compositions described herein may be provided as liquid suspensions, lyophilized or freeze dried powders or frozen concentrates for addition to target regions other than a subject.

The strains or compositions are capable of reducing colonization of pathogenic bacteria in the gastrointestinal tract of the subject. The gastrointestinal tract includes any portion of the gastrointestinal tract. For example, the method may result in a reduction of pathogenic bacterial colonization of the mouth and thus prevent the formation of cavities. Alternatively, the methods may reduce pathogenic bacterial colonization of a portion of the gastrointestinal tract, such as the ceca or ileum of a chicken. In the Examples, the bacterial strains were shown to reduce the colonization of *Campylobacter* in the ceca of chickens.

Reductions in pathogenic bacterial colonization may be determined by comparing the concentration, i.e. the number or colony forming units, of the pathogenic bacteria in a treated subject to that in a control subject that was not administered the strains or compositions described herein. The concentration of the pathogenic bacteria in the gastrointestinal tract (or in a portion of the gastrointestinal tract) of the subject may be determined using a variety of assays available to those skilled in the art. The portion of the gastrointestinal tract of interest may be harvested from the animal, washed or scraped to collect bacteria and then the concentration of bacteria determined using techniques such as differential plating and colony forming unit analysis, real-time PCR for the pathogenic bacteria, microscopic determination using stains or dyes specific for the pathogenic bacteria or other assays.

The methods may result in a significant reduction in the pathogenic bacterial colonization of the subject as compared to control subjects. Suitably pathogenic bacterial colonization is reduced by at least 15%, 20%, 25%, 30%, 35%, 40%, 45%, 50% or even more. Pathogenic bacterial colonization may be reduced by 2-fold, 3-fold, 5-fold, 10-fold, 15-fold, or even 20-fold. The pathogenic bacterial load may be reduced by 1 log, 2 logs, 3 logs, 4 logs or even 5 logs as compared to the pathogenic bacterial load in a control subject not treated with at least one of the ME-1, ME-2 or ME-3 bacterial strains or another enhanced motility strain selected by the methods described herein or a composition comprising at least one of these strains. The method may be used prophylactically to prevent, infection or colonization with a pathogenic bacterium. Prophylactic administration requires that at least one of the ME-1, ME-2 or ME-3 bacterial strains or another enhanced motility strain selected by the methods described herein or a composition comprising at least one of these strains is administered to the subject prior to the subject's colonization with the pathogenic bacteria.

Alternatively the method may be used to decrease bacterial load after colonization or infection with pathogenic bacteria. A variety of methods may be used to determine if a subject has been exposed to or is colonized with a pathogenic bacterium. For example, an immunoassay of the subject's blood may demonstrate prior exposure to a bacterial pathogen by the presence and ability to detect antibodies directed against the pathogen. The subject's saliva or feces may also be tested for the presence of the pathogenic bacteria prior to initiation of the methods. In the Examples, the chicks were administered the bacterial strains prophylactically on the day of hatch, such that prior exposure to the pathogenic bacterium was minimized.

The following examples are meant to be illustrative of the invention as described and claimed and are not meant to limit the scope of the invention. All references cited herein are hereby incorporated by reference in their entireties.

EXAMPLES

Materials and Methods

Isolation Studies
Probiotic Collection Study

Day-old broiler chicks (n=80) were obtained from a commercial hatchery and placed into floor pens with dimensions of 3.06 m$^2$ (33 ft$^2$) previously equipped with fresh litter (pine shavings) and heaters. Birds in this and subsequent trials had ad libitum access to both feed (diet formulated to meet or exceed the requirements of the NRC) and water during all trials. At 2 weeks of age the birds were euthanized using $CO_2$ and ceca collected.
Identification and Selection of Isolates Euthanized chicks were placed on a surgical board, the abdominal feathers were removed, and the skin was disinfected with 70% alcohol. A 5 cm incision was made on the abdominal skin and the ceca were removed. The ceca from each bird was placed into a sterile bag and individually stored at −80° C. (VWR Forma Scientific, Inc, Ohio) until analysis. The ceca were thawed and the contents were squeezed into sterile tubes and diluted with Butterfield's Phosphate Diluent (BPD—Difco, Becton Dickison, Md.) in three ten-fold dilutions. One hundred μL of each solution was spread on Blood Agar Plates (BAP—Difco, Becton Dickison, Md.), and the plates were aerobically incubated for 24 h at 37° C., Isolated colonies were picked and streaked onto Tryptic soy agar (TSA; EMD, N.J.) to assure purity and incubated aerobically at 37° C. for 24 h. Single, isolated colonies were individually grown in 5 mL of Tryptic Soy Broth (TSB—Difco, Becton Dickison, Md.) for 8 h or until turbid. Bacteria were identified using the Biolog® system (Biolog, inc., Hayward, Calif.; Holmes et al., J. Clin. Microbiol. (1994) 32(8):1970-1975; Kersters et al., 1997, *Utility of the Biolog system for the characterization of heterotrophic microbial communities.* 20:3, 439-447), Stocks of those bacteria were prepared by centrifuging TSB at 3000 rpm for 10 rain, pouring off supernatant and resuspending in 2 mL TSB with 20% filter-sterilized glycerol. The suspensions then were dispensed into 1 mL aliquots and stored at −80° C.

Further selection of isolates was conducted by using three criteria: 1) identifying those isolates Generally Recognized as Safe (GRAS) based on the FDA list; 2) identifying which of these GRAS isolates demonstrated motility characteristics; and 3) determining which of the motile, GRAS isolates were capable of inhibiting *Campylobacter* growth in vitro. To determine motility characteristics GRAS isolates were inoculated in Sulfide Indole Motility (BBL™ SIM medium, Becton-Dickinson) in a sterile tube and incubated for 24 hours at 37° C. The bacteria were considered motile if migration away from the line of inoculation occurred. Those bacteria positive for motility were further tested in vitro against *Campylobacter* using the soft agar overlay technique to detect antimicrobial activity (Fredericq, Annu. Rev. Microbiol (1957) 11:7-22; Miyamoto et al., Poult. Sci. (2000) 79:7-11 and Zhang et al., J. Food Prot. (2007) 70(4):867-873). The selected isolates were tested against four strains of wild type *Campylobacter jejuni* isolated from chickens and one ATTC strain as previously described by this laboratory (Farnell et al., J. Appl. Microbiol. (2005) 99:1043-1050). Briefly, 10 μL loops of each frozen strain were cultured into 5 mL *Campylobacter* enrichment broth (CEB; International Diagnostics Group, Lancaster, England) and incubated for 48 h at 42° C. For the second passage, again 10 μL loops from each strain were transferred into fresh 5 mL CEB and incubated for 24 hours at 42° C. under microaerophilic conditions (5% $O_2$, 10% $CO_2$, and 85% $N_2$). Following incubation, the strains were pooled in a 25 mL tube and 3 mL were transferred into a glass tube to be read in a spectrophotometer to determine the concentration of bacteria present in the culture. After measuring the absorbance (OD), the tube containing the culture was centrifuged at 3,500×g for 10 min. The supernatant was discarded and the pellet was resuspended in an equal amount of Butterfield's Phosphate Diluent (BPD). The culture was serially diluted to obtain an inoculum with a desired concentration of 4×10$^5$ cfu/mL. Detection of *Campylobacter* inhibition was assessed by measuring the inhibition zone surrounding the isolate colonies on the plate.
Selection for Motility Enhancement The GRAS isolates demonstrating motility characteristics and the ability to inhibit *Campylobacter* in vitro were further selected for motility enhanced characteristics. Isolates were incubated in TSB for 24 hours at 37° C. Bacteria were transferred into motility test plates (modification from Tittsler and Sandholzer (J. Bacteriol. (1936) 31(6): 575-580) by adding TTC; BBL™ Motility Becton-Dickinson). The plates were incubated for 24 hours at 37° C. Migration capability was detected by measuring the diameter of dispersion from the initial point. If the dispersion was not concentric, the measurements were based on the farthest colonies present at the extremes. The diameter was measured and recorded in each pass and, after the last pass the identities of isolates were confirmed using the Biolog® system. The farthest colony from the center was picked using a sterile loop and incubated in TSB at 37° C. overnight. The procedure was repeated ten times to further select colonies with best migration capability. The bacterial isolates obtained from the last passage were identified as motility enhanced (ME) isolates.

The ME isolates demonstrating the greatest motility in vitro (colonies with the largest diameters from the initiation point on the last passage) were used in field trials. For study purposes these strains were designated as ME isolate 1, 2 or 3.
Animal Studies 
In Vivo Testing of Motility Enhanced Isolates against *Campylobacter*

Three trials were conducted using one-day-old chicks. In each trial 80 broilers were randomly allocated into 8 separated floor pens (10 birds/pen) for 14 days and one of eight treatments was randomly assigned to each pen. The treatments groups included positive controls (*Campylobacter*, no probiotic) or probiotics given individually (isolates 1, 2 or 3 ME) or in combinations (isolates 1 and 2; 1 and 3; 2 and 3; or a combination of the three isolates ME). At day of hatch, bacterial isolates were administrated to each chick by oral gavage consisting of 0.25 mL of TSB broth with approximately $10^7$ cfu/mL. At day seven, all chicks (including the positive control), were challenged via oral gavage (0.25 mL) with a solution of BPD containing approximately $4\times10^5$ cfu/mL of a mixture of the four strains of *Campylobacter*. At 2 weeks of age chicks were euthanized using $CO_2$ and ceca collected to assess *Campylobacter* colonization.

In Vivo Comparison of Motility Enhanced Isolate against *Campylobacter*

The ME probiotic isolate that offered the most consistent reduction during field testing was chosen to be further tested against its original strain in an in vivo study. Three trials were conducted. In each trial, 30 chicks (n=10/treatment) were randomly allocated into 3 separated floor pens for 14 days. The birds were assigned to treatment groups: 1) positive controls (*Campylobacter*, no probiotic); 2) original strain of isolate 1 not subjected to ME, also designated original strain; or 3) isolate I-ME (pass 10, after enhancement of motility characteristics). At-day-of-hatch probiotic treatment groups were inoculated by oral gavage (0.25 mL) with approximately $10^7$ cfu/mL of the appropriate bacteria culture. On day seven all groups were challenged by oral gavage with a solution of approximately $4\times10^5$ cfu/mL containing the four strains of *Campylobacter*. At 2 weeks of age chicks were euthanized using $CO_2$ and ceca collected to assess *Campylobacter* colonization.

Enumeration of *Campylobacter* in Cecal Contents

Cecal *Campylobacter* concentrations were enumerated by the procedure of Cole and co-workers (Poult. Sci. (2006) 85:1570-1575). Briefly, ceca from each bird were transferred to a sterile plastic bag and the contents squeezed into 15-mL tubes and serially diluted (1:10) with BPD and inoculated on labeled Campy-Line Agar (CLA) plates. The CLA plates were incubated for 48 h at 42° C. under microaerophilic conditions. Direct bacterial counts were recorded and converted to cfu/mL of the cecal content. *Campylobacter* colonies were confirmed by latex agglutination test (PANBIO, INC. Columbia, Md.) and further identified as *Campylobacter jejuni* using API® Campy (Biomerieux® Durham, N.C.; ATCC 33291 strain used as control).

Statistical Analysis

Data were analyzed using ANOVA with the GLM procedure (SAS Institute, 2002). For field trials, the number of *Campylobacter* colonies were logarithmically transformed (log 10 cfu/mL) before analysis to achieve homogeneity of variance (Byrd et al., Poult. Sci. (2003) 82:1403-1406). Treatment means were partitioned by LSMEANS analysis (SAS Institute, 2002, SAS/STAT® User's guide: Release 9.03 edition. SAS Institute Inc., Cary, N.C.). A probability of $P<0.05$ was required for statistical significance.

Results

Isolation Studies

In the original probiotic isolation studies, 139 bacteria were isolated from the ceca. Of these, 39 isolates were verified to be GRAS. Six of the GRAS isolates were positive for initial motility characteristics. Three out of six were different strains of *Bacillus subtilis* ssp.

Selection for Motility Enhancement

Five out of the six motile, GRAS isolates demonstrated inhibition against *Campylobacter jejuni* in vitro (FIG. 1). Not all isolates presented the same progress during the selection for motility enhancement. Some of the isolates had their best performance within passes rather than the last pass such as isolate 1 (pass 4), isolate 2 (pass 9), isolate 3 (pass 6), isolate 4 (pass 1) and isolate 5 (pass 3). In order to standardize the procedure the number of passes was limited to 10 and the selection was based on the size of the diameter in the last pass. By using this criterium 3 out of 5 initial isolates presented the largest spread in pass 10. For study purposes these strains were designated as ME: isolate 1, isolate 2 and isolate 3.

Study 1: In Vivo Testing of Motility Enhanced Isolates against *Campylobacter*

Cecal *Campylobacter* counts for the positive control group averaged approximately $2\times10^7$ cfu/g in the three field trials (FIG. 2). Isolate 1 and isolate 2 reduced *Campylobacter* counts ($P<0.05$) in cecal contents when compared to the positive control in 2 out of 3 trials (FIG. 2). Significant reductions were also found in 1 out of 3 trials for triple combination (1&2&3) and dual combination (1&2), Trials 1 and 3, respectively. Among them isolate 1-ME presented the most consistent reduction, in 2 out of 3 trials, being selected for a further study.

Study 2: In Vivo Comparison of Motility Enhanced Isolate against *Campylobacter*

Cecal *Campylobacter* counts for positive control group averaged approximately $2\times10^7$ cfu/g for all in vivo trials. For all three trials conducted (FIG. 3), isolate 1-ME consistently reduced *Campylobacter* cecal counts when compared to the positive control group, and resulted in lower *Campylobacter* cecal counts when compared to the non-motility enhanced isolate 1. The cecal *Campylobacter* counts for non-motility enhanced isolate 1 did not differ from the positive control in all trials.

Selecting mottle GRAS bacteria from cecal contents and further selection for their migration capability resulted in isolation of a probiotic bacterium capable of consistently outcompeting *Campylobacter* for binding sites in in vivo trials (FIG. 2). *Campylobacter* ssp. is predominantly found in the lower gastrointestinal tract, concentrated in the deep mucus layer of the cecal crypts. One of the possible mechanisms by which some of the ME isolates contributed to the reduction in *Campylobacter* counts may lay in their ability to get to the intestinal niche occupied by *Campylobacter* and compete for nutrients and binding sites.

The motility enhanced isolates were all identified as *Bacillus subtilis*. The genus *Bacillus* comprises a diverse collection of aerobic endospore-forming, motile bacteria. *Bacillus subtilis* as well *Bacillus licheniformis* species are on the Food and Drug Administration's GRAS list. They have been widely used in the food industry for production of enzymes such as cellulose and expression of thaumatin II, a sweet-tasting protein, non-caloric substitute for sugar and in Japan were *B. subtilis* is used to produce fermented soybean products. The use of *Bacillus* as a probiotic could have more than one mode of action, including competitive exclusion for adhesion sites and production of antimicrobial agents such as bacteriocins.

We claim:

1. A method of selecting a first bacterium capable of reducing pathogenic bacterial colonization by a second bacterium in the intestinal tract of a subject comprising: (a) selecting bacterial isolates identified as Generally Regarded as Safe bacteria by the Food and Drug Administration; (b) selecting motile bacterial isolates from the bacterial isolates of step (a); (c) selecting the bacterial isolates of step (b) that are capable of inhibiting the growth of *Campylobacter* in vitro; (d) inoculating the bacteria selected in step (c) on motility agar plates and incubating the bacteria on the motility agar plates for 24 hours at 37° C.; (e) selecting the farthest migrating bacterial colony from the point of inoculation and (f) repeating steps (d) and (e) with the farthest migrating bacterial colony of step (e) to select the first bacterium, wherein the first bacterium is capable of migrating at least 0.75 cm from the point of inoculation on the motility agar plates after incubation for 24 hours at 37° C. and wherein the first bacterium is capable of reducing pathogenic bacterial colonization by a second bacterium when the second bacterium encounters the first bacterium in the intestinal tract of a subject.

2. The method of claim 1, wherein in step (c) of claim 1 soft agar overlay technique is used to assess antimicrobial activity against *Campylobacter* and bacterial isolates capable of inhibiting the growth of *Campylobacter* in vitro are selected.

3. The method of claim 1, wherein the first bacterium is selected from the group of genera consisting of *Eschenchia, Salmonella, Shigella, Bacillus, Clostridium* and *Bacteroides*.

4. The method of claim 1, wherein the second bacterium comprises a bacterium selected from the group of genera consisting of *Campylobacter, Salmonella* and *Escherichia*.

5. The method of claim 1, wherein the first bacterium is capable of reducing colonization by *Campylobacter* in the subject.

6. The method of claim 1, wherein the subject is a poultry animal, cow, human or pig.

7. The method of claim 1, wherein the first bacterium is capable of migrating at least 1.5 cm from the point of inoculation on the motility agar plates after incubation for 24 hours at 37° C. or is capable of migrating to create a zone of growth of having a diameter of at least 3 cm, based on the farthest migrating bacteria, centered on the point of inoculation on the motility agar plates after incubation for 24 hours at 37° C.

8. The method of claim 1, wherein the first bacterium is capable of migrating to create a zone of growth of having a diameter of at least 1.5 cm centered on the point of inoculation on the motility agar plates after incubation for 24 hours at 37° C.

* * * * *